US007227358B2

(12) United States Patent
Lehtonen-Krause

(10) Patent No.: US 7,227,358 B2
(45) Date of Patent: Jun. 5, 2007

(54) MR METHOD AND APPARATUS FOR DETERMINING CORONAL AND SAGITTAL IMAGE PLANES FROM AN IMAGE DATA SET OF A SHOULDER JOINT

(75) Inventor: Sari Lehtonen-Krause, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 22 days.

(21) Appl. No.: 11/220,221

(22) Filed: Sep. 6, 2005

(65) Prior Publication Data

US 2006/0079760 A1   Apr. 13, 2006

(30) Foreign Application Priority Data

Sep. 6, 2004   (DE) ...................... 10 2004 043 058

(51) Int. Cl.
  *G01V 3/00* (2006.01)
(52) U.S. Cl. ...................................... 324/307; 600/410
(58) Field of Classification Search ................ 324/307, 324/309; 600/410, 425; 382/203, 206
See application file for complete search history.

(56) References Cited

U.S. PATENT DOCUMENTS

| 6,487,432 | B2 * | 11/2002 | Slack .......................... 600/407 |
| 6,799,066 | B2 * | 9/2004 | Steines et al. ............... 600/407 |
| 6,844,884 | B2 * | 1/2005 | Balloni et al. .............. 345/629 |
| 2005/0197562 | A1 * | 9/2005 | Graessner ................... 600/410 |
| 2005/0203381 | A1 * | 9/2005 | Harder ........................ 600/420 |
| 2005/0228254 | A1 * | 10/2005 | Torp et al. ................... 600/407 |

OTHER PUBLICATIONS

"Normal Shoulder: MR Imaging," Kieft et al., Radiology, vol. 159, No. 3 (1986) PP. 741-745.
"Acromial Shapes and Extension of Rotator Cuff Tears: Magnetic Resonance Imaging Evaluation," Hirano et al., Journal of Shoulder and Elbow Surgery, vol. 11, No. 6 (2002), pp. 576-578.
"Interactive Contour Detection in Tomographic Data," Kaptein et al., Proceedings of the 18th Annual International Conference of the IEEE, Engineering in Medicine and Biology Society (1996), vol. 3, pp. 1047-1048.

* cited by examiner

*Primary Examiner*—Louis M. Arana
(74) *Attorney, Agent, or Firm*—Schiff Hardin LLP

(57) ABSTRACT

In a method for determination of coronal and sagittal planes for the subsequent acquisition of new magnetic resonance slice images or the representation of magnetic resonance slice images from an existing image data set of a shoulder joint starting from a data set representing a transversal slice image of a shoulder joint, the slice image is analyzed using at least one analysis algorithm to determine the shoulder blade and for two points lying on the shoulder blade that define the coronal plane. The slice image also is analyzed using at least one analysis algorithm to identify the shoulder blade and the half-moon-shaped arc of the joint connection between the had of the upper extremity of the humerus and the shoulder blade, and two points on the arc in the region of the joint connection with the shoulder blade that define the sagittal plane. A coronal slice image or a sagittal slice is then acquired or represented at the display dependent on the orientation of the identified planes.

7 Claims, 4 Drawing Sheets

MR METHOD AND APPARATUS FOR DETERMINING CORONAL AND SAGITTAL IMAGE PLANES FROM AN IMAGE DATA SET OF A SHOULDER JOINT

BACKGROUND OF THE INVENTION

1. Field of the Invention

The present invention concerns a method for determining of distinguished coronal and sagittal planes from an already-present image data set of a shoulder joint for the subsequent acquisition of new magnetic resonance slice images or the representation of magnetic resonance slice images.

2. Description of the Prior Art

Diseases in the region of the shoulder joint are painful and impair the patient in terms of freedom of movement. Magnetic resonance tomography is a gentle method for examination of the shoulder joint. In order to acquire an optimally large amount of information from the examination region, so as to be able to generate meaningful slice image therefrom, the shoulder joint is acquired in the form of a number of slice image sets that are respectively acquired in specific planes. The data acquisition ensues in the transversal, coronal and sagittal directions, but these planes need not be exactly perpendicular to one another but can, if applicable, be tilted relative to one another. Each slice image set is composed of, for example, twenty to forty individual slice images that all have been acquired in parallel slice planes abutting one another. The entire examination volume can be acquired in this manner.

Difficulties arise, however, when a follow-up examination is to ensue at a later point in time in order to implement therapy monitoring. Because the individual slice image groups, or the various measurement protocols (for example T1 or T2), typically are set manually in coronal, sagittal and transversal orientation by the apparatus operator (technician), difficulties occur with regard to reproducing the original slice plane positioning. This applies even when the same operator does the setting at a later point in time, but is particularly a problem when a different operator acquires the later data. The slice images previously acquired do not normally exist as references, such that the later technician cannot make use of them for orientation purposes.

Similar problems also occur when acquired slice images are to be evaluated at a later point in time. Here as well each image representation ensues using slice images in coronal, transversal or sagittal orientations. Depending on how the diagnosing physician now places the respective orientation, different plane orientations and therewith different image representations can occur. Again, no reproducibility is achieved.

SUMMARY OF THE INVENTION

An object of the present invention is to provide a method that enables a reproducible plane determination of the coronal and sagittal planes under the above-described circumstances in order to enable a reproducible slice image acquisition or slice image representation.

The above object is achieved in accordance with the invention by a method of the previously-described type wherein, starting from a data set representing a transversal slice image of a shoulder joint, this slice image is analyzed using at least one analysis algorithm to identify the shoulder blade and two points lying on the shoulder blade that define the coronal plane, and wherein the slice image also is analyzed using at least one analysis algorithm to identify the shoulder blade and the half-moon-shaped arc of the joint connection between the head of the upper extremity of the humerus and the shoulder blade and two points on the arc in the region of the joint connection with the shoulder blade (thus on the arc edges in the transition region to the shoulder blade), these points defining the sagittal plane.

Coronal or sagittal slice images then are acquired or represented at orientations dependent on the aforementioned identified planes.

Using one or more analysis algorithms, in the inventive method the identified anatomical structures of the shoulder joint can be unambiguously identified in the transversal slice image and used for subsequently determining the plane. For this purpose, the shoulder blade that is visible in the transversal slice image is inventively identified. Via the analysis algorithm it can be defined which region of the shoulder blade appearing as a transversal section is relevant in order to place the plane therethrough. The lateral should blade section or its edge is preferably identified. The coronal plane is now placed along a straight line through the shoulder blade, and thereby the entire examination volume is placed along this edge, or using two distinguished points that are determined by the algorithm.

In a second step, the transversal slice image is analyzed using (likewise) at least one analysis algorithm (which can be the same analysis algorithm used for the first analysis, or a different analysis algorithm) for determination of the half-moon-shaped arc of the joint connection between the head of the upper extremity of the humerus and the shoulder blade. This half-moon-shaped arc is clearly prominent in the transversal exposure. Two points lying on the arc are now likewise determined, primarily in the transition region to the shoulder blade, thus on the arc edges. A line that defines the sagittal plane is now likewise placed through these two points.

Now the coronal and the sagittal planes are defined in addition to the already-known transversal plane, exclusively using anatomical structures that are typical for the shoulder joint. A subsequent image acquisition can now ensue on the basis of these automatically determined planes, just as corresponding slice images along these planes can be determined form an already-acquired three-dimensional image data set.

The fact that anatomical landmarks are used for automatic plane determination allows a reproducible determination of the planes. Generally, the anatomy in question does not change. The only is a requirement is that the transversal slice image exposure, which is the basis for the anatomy analysis, be essentially the same in the follow-up exposures. This is also true in the case of a reproducible image representation from already-present image data. Here as well, a subsequent evaluation can always ensue using images that reproducibly lie in the same plane as in the first evaluation.

In an embodiment of the invention, the middle point of the of the upper arm bone joint head shown in the transversal slice image is identified for a subsequent slice image acquisition after the determination of the coronal or the sagittal plane using at least one analysis algorithm, through which middle point the determined coronal and sagittal planes are placed that serve as central planes for the subsequently-acquired planes of parallel slice images. This embodiment of the invention enables the coronal plane and the sagittal plane to serve as a center plane for the acquisition of subsequent planes of parallel slice image families. A previously-determined coronal or sagittal plane is inventively shifted in a plane-parallel manner into the middle of the head of the upper extremity of the humerus (which is determined by an analysis algorithm) likewise serving as an anatomical landmark. This plane forms the central plane for the later slice images that are subsequently acquired on both sides of this in parallel planes. The determination of the center of the head of the upper extremity of the humerus is likewise automatically possible without anything further using the analysis algorithm because the bone head is essentially visible round in the transversal slice image. For this a circular line approximating the contour or edge shape of the head of the upper extremity of the humerus shown in the transversal section image, for example, can be virtually (i.e. computationally) placed around the joint head whose middle point will be determined. This can automatically occurs with an image processing device that embodies a hardwired or programmed computer that also effects the other analyses. This embodiment of the invention thus enables an automatic central plane determination. Alternatively, starting from the determination of both coronal and sagittal orientation planes, the diagnosing physician can determine in which direction the examination volume should be acquired, starting from both of these orientation planes.

In accordance with the invention the transversal slice image that is the basis for the anatomy analysis can be selected from a family acquired immediately beforehand, or a pre-existing family of slice images acquired in an examination volume in the shoulder joint region. This slice image selection can ensue manually or automatically, meaning that the transversal plane can be determined automatically or manually.

The above object also is achieved in accordance with the invention by a magnetic resonance system fashioned for implementation of the method described above.

DESCRIPTION OF THE PREFERRED EMBODIMENTS

Figure 1:
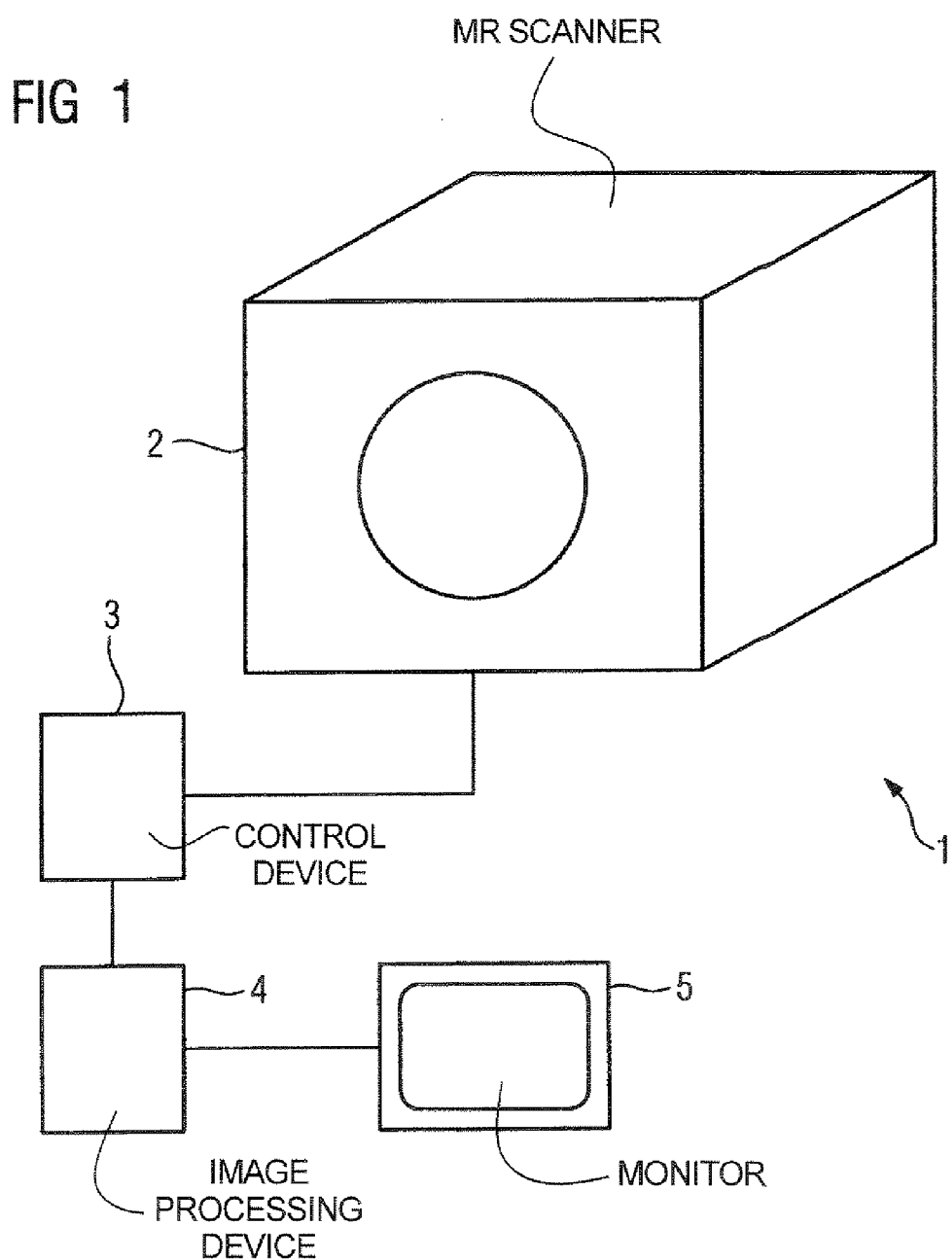
FIG. 1 is a schematic block diagram illustrating the basic components of a magnetic resonance imaging system constructed and operating in accordance with the present invention.

FIG. 1 shows an inventive magnetic resonance system 1 formed by an MR scanner 2 connected to a control device 3 (controlling the operation thereof) with an associated image processing device 4, that includes a suitably fashioned or programmed calculation device. The control device 3 controls the entire operation flow, including the image acquisition. The image processing ensues in the image processing device 4 connected to a monitor 5 for image display.

For a shoulder joint examination, three localizer exposures (overview images) are initially acquired as is typical in three defined orthogonal orientations of the shoulder joint region. These localizer exposures serve for the generation of a rough overview image. A transversal plane that runs through the shoulder joint is now automatically determined using these localizer exposures. A first transversal slice image family is now automatically acquired based on this automatically-determined alignment of the transversal plane. These transversal slice images, for example twenty to forty individual images, as a whole describe the examination volume (thus the shoulder joint). An identified slice image in which specific anatomical structures are visible is now (preferably automatically) selected from this transversal slice image family; this selection being explained with regard to FIGS. 2 through 4. The selection can ensue specifically with regard to the sought and required structures, i.e. the slice image best suited for the analysis to be implemented is selected.

Figure 2:
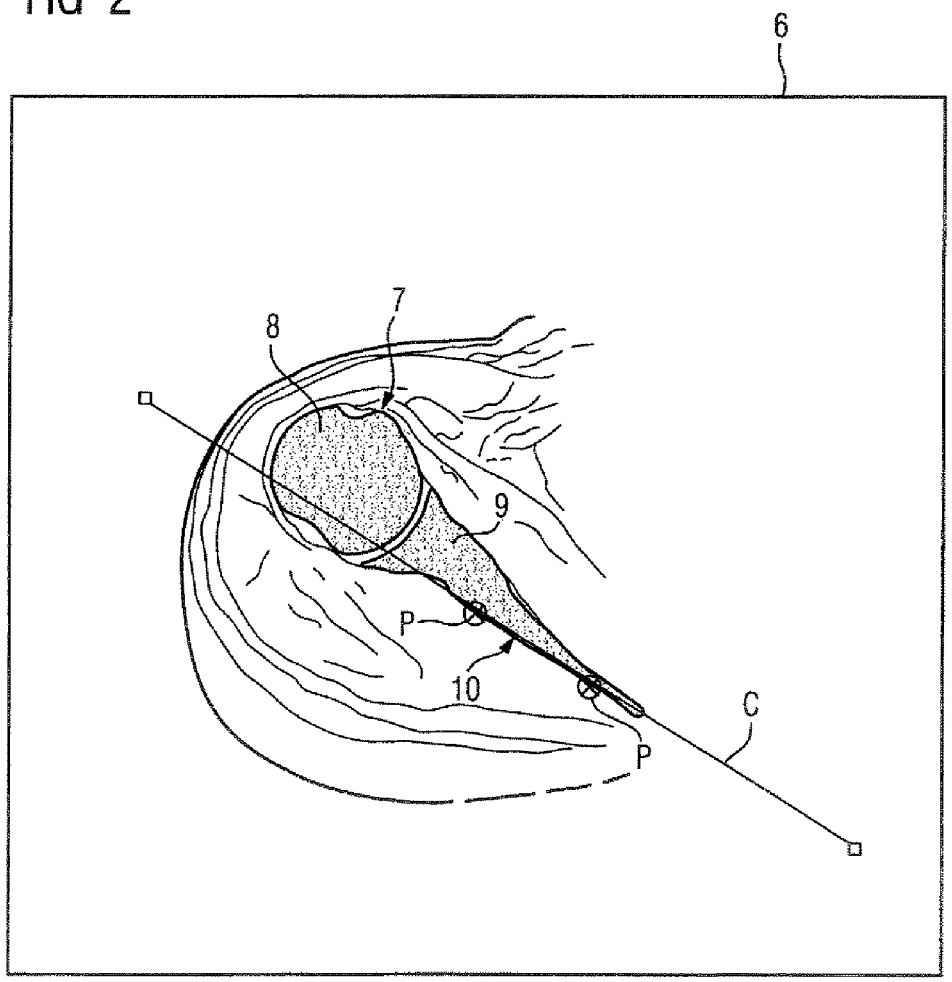
FIG. 2 illustrates a displayed representation of a shoulder joint for explaining determination of the coronal plane in accordance with the present invention.

FIG. 2 shows a selected transversal slice image 6 as a transversal section through the shoulder joint 7 of a patient. The head of the upper extremity of the humerus 8 as well as the shoulder blade 9 (the socket in which the head of the upper extremity of the humerus 8 is accommodated is not shown in detail in this section).

In a first method step, the shoulder blade 9 is now determined, for example by an edge analysis of the slice image 6, using an analysis algorithm. A specific, identified shoulder blade section (here the lateral section 10 describing a straight edge) is automatically determined. Two points P that are respectively marked by a cross are automatically defined on this section. A straight line or line C that describes the orientation of the coronal plane is now placed through these two points P.

Figure 3:
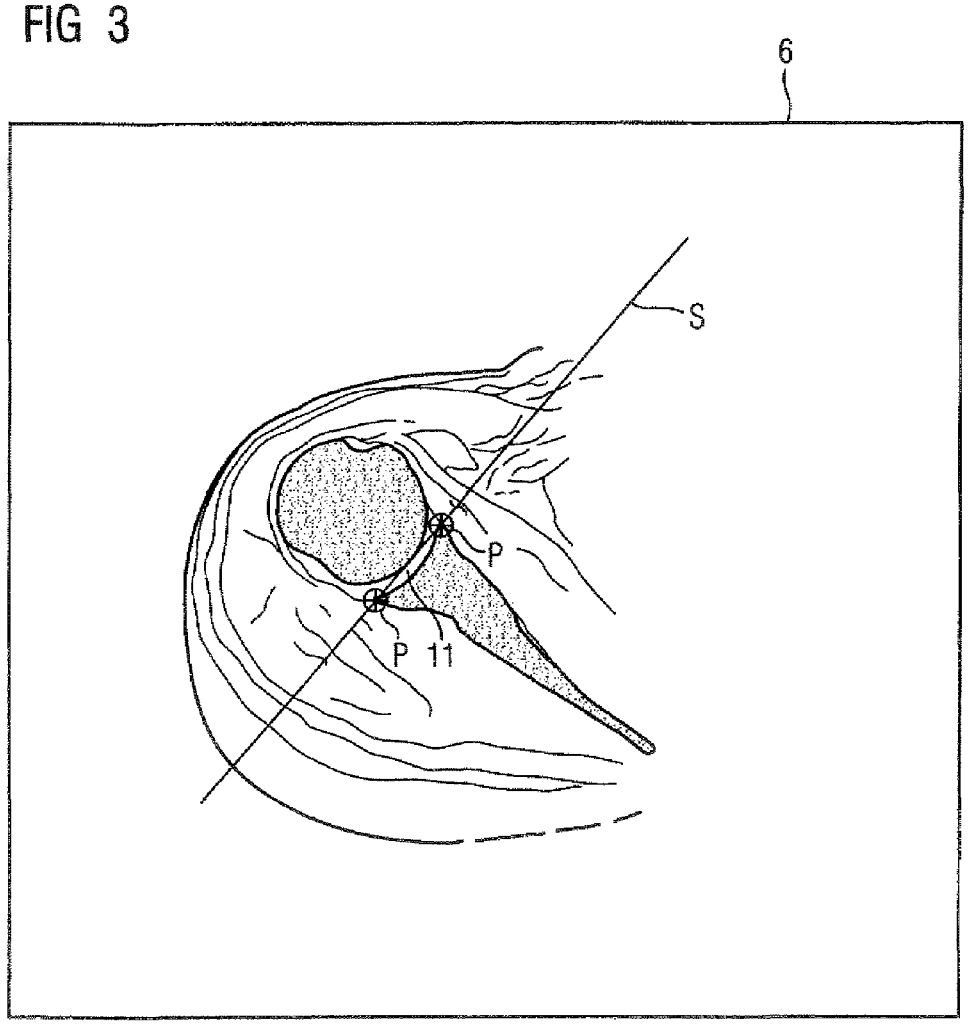
FIG. 3 illustrates a displayed representation of a shoulder joint for explaining determination of the sagittal plane in accordance with the present invention.

The half-moon-shaped arc 11 of the shoulder blade is determined in a second step (see FIG. 3). This arc 11 is very easily recognizable; it is ultimately formed by the cartilaginous substance of the shoulder blade. At the ends of the arc 11, two points P (respectively shown by a cross) are also determined on the arc 11, through which points P the line S (likewise a straight line) is placed that determines the orientation of the sagittal plane.

Figure 4:
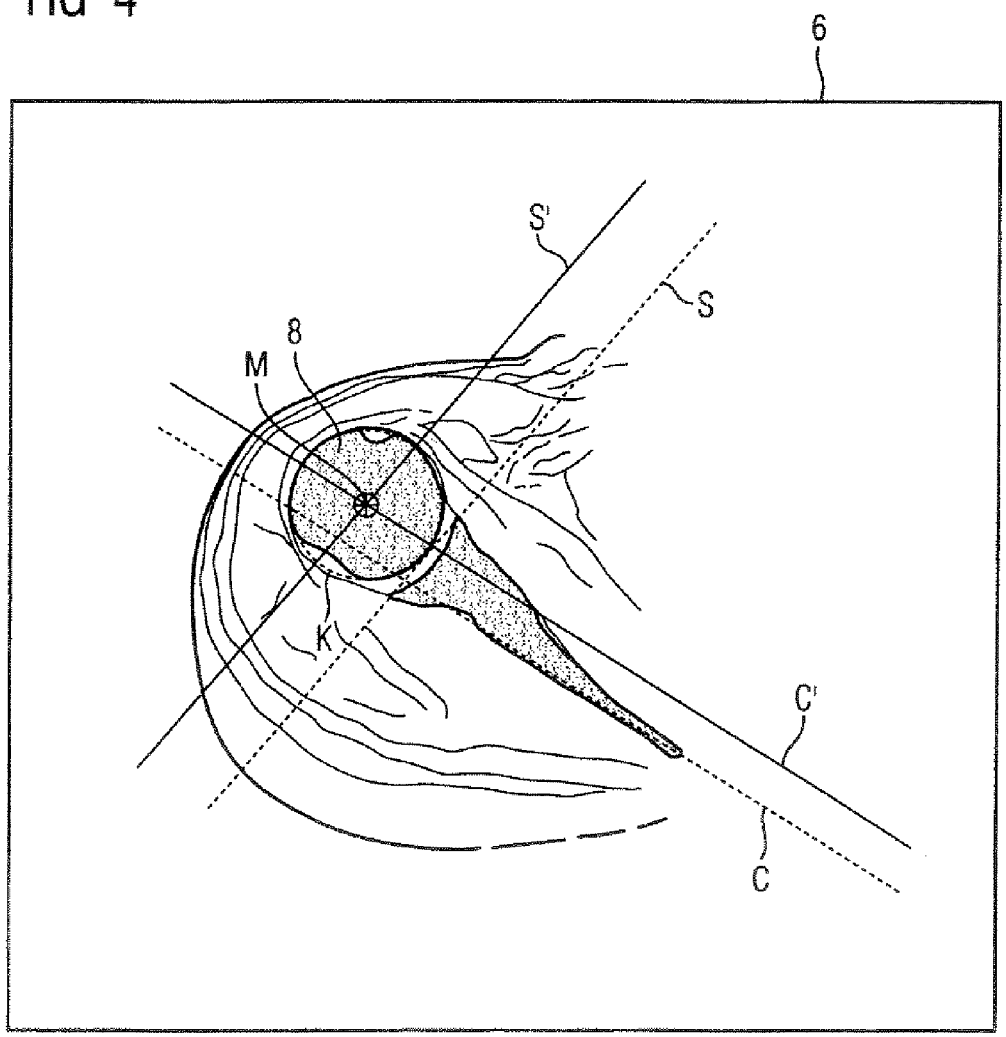
FIG. 4 illustrates a displayed representation of a shoulder joint for explaining determination of the coronal and sagittal central planes in accordance with the present invention.

In a third step, the upper arm bone joint head 8 (shown round in the transversal image) and a circular line K approximating its contour are now likewise determined using an analysis algorithm. The circular line K as well as its middle point M (that is likewise represented by a cross) is determined. The previously-determined lines C and S are now shifted in a plane-parallel manner until they proceed through the middle point M, as is indicated in FIG. 4 by the lines C' and S'. These lines C' and S' define the position of the coronal and sagittal central planes. Starting from these central planes, the further slice images are acquired in a subsequent image acquisition on both sides of the identified central plane and the examination volume is acquired in its entirety in a plane-specific manner.

As described, a reproducible plane determination is inventively determined solely using distinguished anatomical shoulder joint structures. The determined coronal and sagittal lines or planes C and S serve for the ultimate plane definition as well as for the correct angulation for the subsequently slice image families to be acquired. The subsequently image acquisition then ensues using the determined planes, controlled by the control device 3 of the magnetic resonance system 1.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method for determining coronal and sagittal planes from a displayed tomographic image of a shoulder joint, comprising the steps of:

displaying a transversal tomographic image of a shoulder joint at a monitor, the displayed image of the shoulder joint arising from an underlying image data set;

electronically analyzing the underlying image data set of the displayed shoulder joint using a first analysis algorithm to identify, in said shoulder joint, the shoulder blade and to identify two points on the shoulder blade defining the coronal plane;

analyzing said underlying data set of said shoulder joint using a second analysis algorithm to identify the shoulder blade and to identify a half-moon shaped arc of the joint connection between the head of the upper extremity of the humerus and the shoulder blade, and to identify two points on said arc at said joint connection that define the sagittal plane; and acquiring tomographic data from, or representing in a further display, at least one of a coronal slice image of said shoulder joint and a sagittal slice image of said shoulder joint, dependent on at least one of the identified coronal plane and the identified sagittal plane.

2. A method as claimed in claim 1 comprising employing the same analysis algorithm as both of said first analysis algorithm and said second analysis algorithm.

3. A method as claimed in claim 1 comprising electronically analyzing said underlying image data set for the displayed image of said shoulder joint, using a third analysis algorithm, to identify a middle point of the head of the upper extremity of the humerus either after identifying said coronal plane or after identifying said sagittal plane, and acquiring tomographic data for a plurality of parallel slice images using said identified coronal plane and said identified sagittal plane proceeding through said middle point as central planes.

4. A method as claimed in claim 1 comprising selecting said transversal tomographic image from a plurality of pre-existing slice images in a family acquired in an examination volume containing said shoulder joint.

5. A method as claimed in claim 4 comprising manually selecting said transverse tomographic image.

6. A method as claimed in claim 4 comprising automatically electronically selecting said transverse tomographic image.

7. A magnetic resonance imaging apparatus comprising:

a magnetic resonance scanner adapted to interact with a subject to acquire magnetic resonance data;

a computer connected to said magnetic resonance scanner to control acquisition of said magnetic data by said magnetic resonance scanner;

a display connected to said computer for displaying a transversal tomographic image of a shoulder joint, the displayed image of the shoulder joint arising from an underlying image data set;

said computer electronically analyzing the underlying image data set of the displayed shoulder joint using a first analysis algorithm to identify, in said shoulder joint, the shoulder blade and to identify two points on the shoulder blade defining the coronal plane;

said computer also analyzing said underlying data set of said shoulder joint using a second analysis algorithm to identify the shoulder blade and to identify a half-moon shaped arc of the joint connection between the head of the upper extremity of the humerus and the shoulder blade, and to identify two points on said arc at said joint connection that define the sagittal plane; and said computer controlling acquisition tomographic data from, or representation in a further display, at least one of a coronal slice image of said shoulder joint and a sagittal slice image of said shoulder joint, dependent on at least one of the identified coronal plane and the identified sagittal plane.

* * * * *